(12) United States Patent
Marshall

(10) Patent No.: US 7,941,226 B2
(45) Date of Patent: *May 10, 2011

(54) MAGNETOSTRICTIVE ELECTRICAL STIMULATION LEADS

(75) Inventor: Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 954 days.

This patent is subject to a terminal disclaimer.

(21) Appl. No.: 11/741,612

(22) Filed: Apr. 27, 2007

(65) Prior Publication Data

US 2008/0269830 A1    Oct. 30, 2008

(51) Int. Cl.
*A61N 1/04* (2006.01)
(52) U.S. Cl. .................. 607/116; 607/2; 607/3
(58) Field of Classification Search .......... 607/2, 3, 607/37, 116, 4, 5, 9
See application file for complete search history.

(56) References Cited

U.S. PATENT DOCUMENTS

| | | |
|---|---|---|
| 4,857,884 A | 8/1989 | O'Malley et al. |
| 5,843,153 A | 12/1998 | Johnston |
| 6,871,091 B2 | 3/2005 | Wilkinson et al. |
| 6,944,489 B2 | 9/2005 | Zeijlemaker et al. |
| 6,985,775 B2 | 1/2006 | Reinke et al. |
| 2007/0141106 A1* | 6/2007 | Bonutti et al. .............. 424/423 |
| 2007/0299490 A1 | 12/2007 | Yang et al. |
| 2008/0269591 A1 | 10/2008 | Halperin et al. |

FOREIGN PATENT DOCUMENTS

| | | | |
|---|---|---|---|
| EP | 0617981 | * | 5/1994 |
| EP | 0617981 A | | 10/1994 |
| WO | 03063946 A1 | | 8/2003 |

OTHER PUBLICATIONS

International Search Report, PCT/US2008/061770, Jul. 8, 2008, 5 Pages.

* cited by examiner

*Primary Examiner* — Carl H Layno
*Assistant Examiner* — Pamela M Bays
(74) *Attorney, Agent, or Firm* — Stephen W. Bauer; Michael J. Ostrom

(57) ABSTRACT

A medical device lead is presented. The medical device lead includes a lead body, an electrode shaft, and a tip electrode. A magnetostrictive element is coupled to the electrode shaft. The magnetostrictive element comprises either terfenol-D and/or galfenol or any material with sufficient magnetostrictive properties. The magnetostrictive element expands when exposed to magnetic resonance imaging.

13 Claims, 11 Drawing Sheets

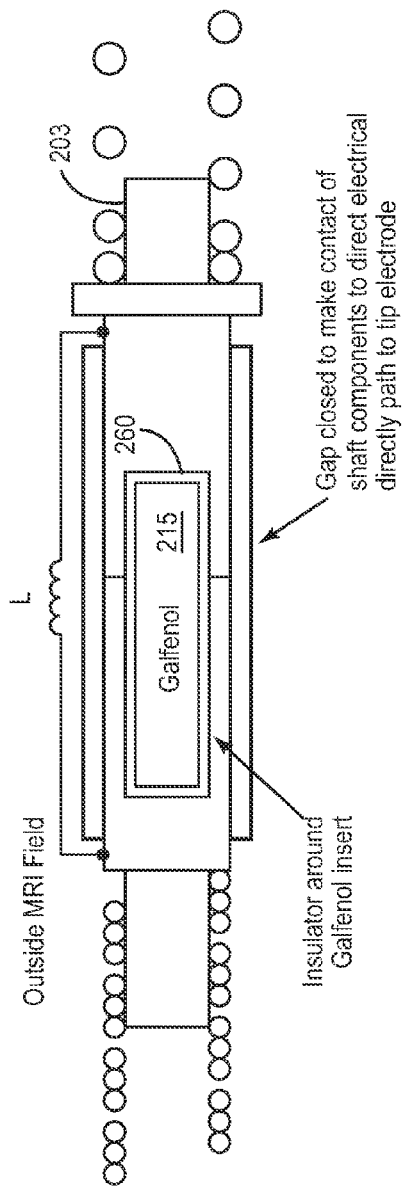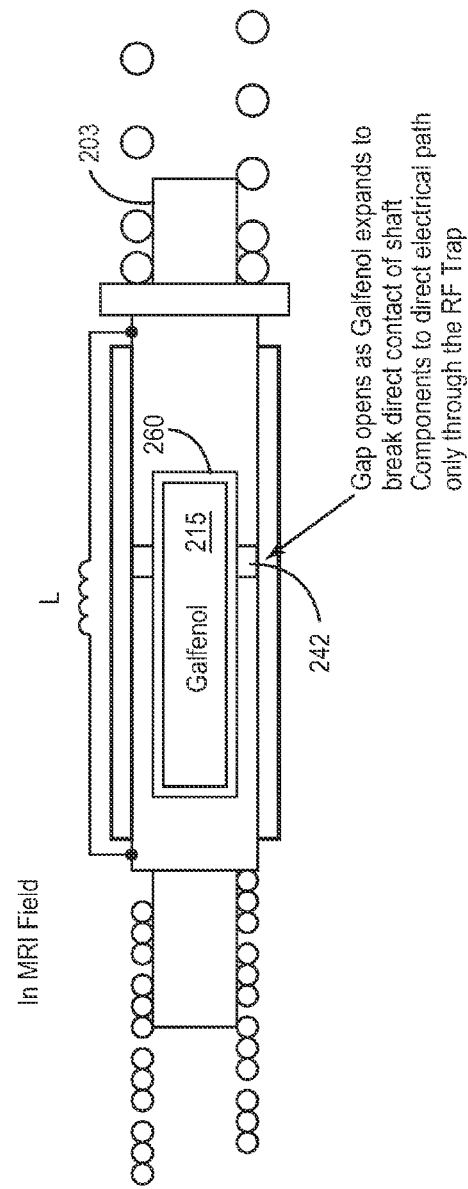
Fig. 7A
Fig. 7B

MAGNETOSTRICTIVE ELECTRICAL STIMULATION LEADS

CROSS REFERENCE TO RELATED APPLICATION

The present invention is a related to another application entitled MAGNETOSTRICTIVE ELECTRICAL STIMULATION LEADS, U.S. application Ser. No. 11/741,601, filed Apr. 27, 2007.

TECHNICAL FIELD

The invention relates to medical devices and, more particularly, to implantable medical device leads for use with implantable medical devices (IMDs).

BACKGROUND

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads are also used for sensing purposes, or for both sensing and stimulation purposes. Implantable leads are also used in neurological devices, muscular stimulation therapy, and devices that sense chemical conditions in a patient's blood, gastric system stimulators.

Occasionally, patients that have implantable leads may benefit from a magnet resonance image being taken of a particular area of his or her body. Magnetic resonance imaging (MRI) techniques achieve a more effective image of the soft tissues of the heart and vascular system. MRI procedures can also image these features without delivering a high dosage of radiation to the body of the patient, and as a result, MRI procedures may be repeated reliably and safely. However, MRI devices may operate at frequencies of 10 megahertz or higher, which may cause energy to be transferred to the lead. In particular, the high frequency fields induce a voltage in the lead, causing the higher potential of the lead to damage the tissue that surrounds the tip electrode of the lead.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein:

FIG. 5A is a schematic diagram of a simplified bipolar circuit for a medical device system;

FIG. 7A depicts a cross-sectional view of an electrode assembly with a magnetostrictive element;

FIG. 7B depicts a cross-sectional view of an electrode assembly with a magnetostrictive element;

DETAILED DESCRIPTION

The present invention is directed to a medical lead, techniques for manufacturing such a lead, and systems that include a medical device coupled to a medical lead according to the present invention. The medical device lead includes a lead body, and electrode shaft and a tip electrode. A magnetostrictive element, coupled to an electrode shaft, serves as an "on/off" switch to manage high frequency signals RF signals (e.g. 21 megaHertz (Mhz) to 128 MHz) generated from a magnetic resonance imaging (MRI) machine away from the tip electrode. The switch is comprised of a magnetostrictive element made of any suitable material with sufficient magnetostrictive properties. Exemplary magnetostrictive material includes terfenol-D or galfenol. Magnetostriction is a property that causes certain ferromagnetic materials to change shape in response to a magnetic field. In particular, the magnetostrictive element expands or contracts. When the lead is not exposed to magnetic resonance imaging (MRI), the magnetostrictive material is contracted. In contrast, when the lead is exposed to MRI, the magnetostrictive material expands. In one embodiment, expansion of the magnetostrictive material causes a first segment to move away from a second segment of the electrode shaft. A gap is created between the first and second segments of the electrode shaft. Therefore, current, induced in the lead due to exposure to the MRI, no longer has a direct electrical path to the tip electrode. Instead, the electrical current induced by high frequency passes through a high impedance component such as a radiofrequency (RF) trap, whereas the low frequency current for sensing and/or pacing is able to pass to and/or from the electrode tip. Consequently, a patient with a medical lead may undergo an MRI procedure without significantly affecting the operation of the medical lead.

In another embodiment, magnetostrictive material is disposed in or near conductive rings that are coupled to the electrode shaft. When the lead is exposed to MRI, the magnetostrictive material expands to create a contact to an additional electrode surface, which allows the induced current to dissipate over a larger surface area. In one embodiment, a tenfold (i.e. 10×) larger surface area ratio results in about tenfold lower temperatures at the tip electrode assuming a ring electrode has low impedance at high frequencies.

Figure 1:
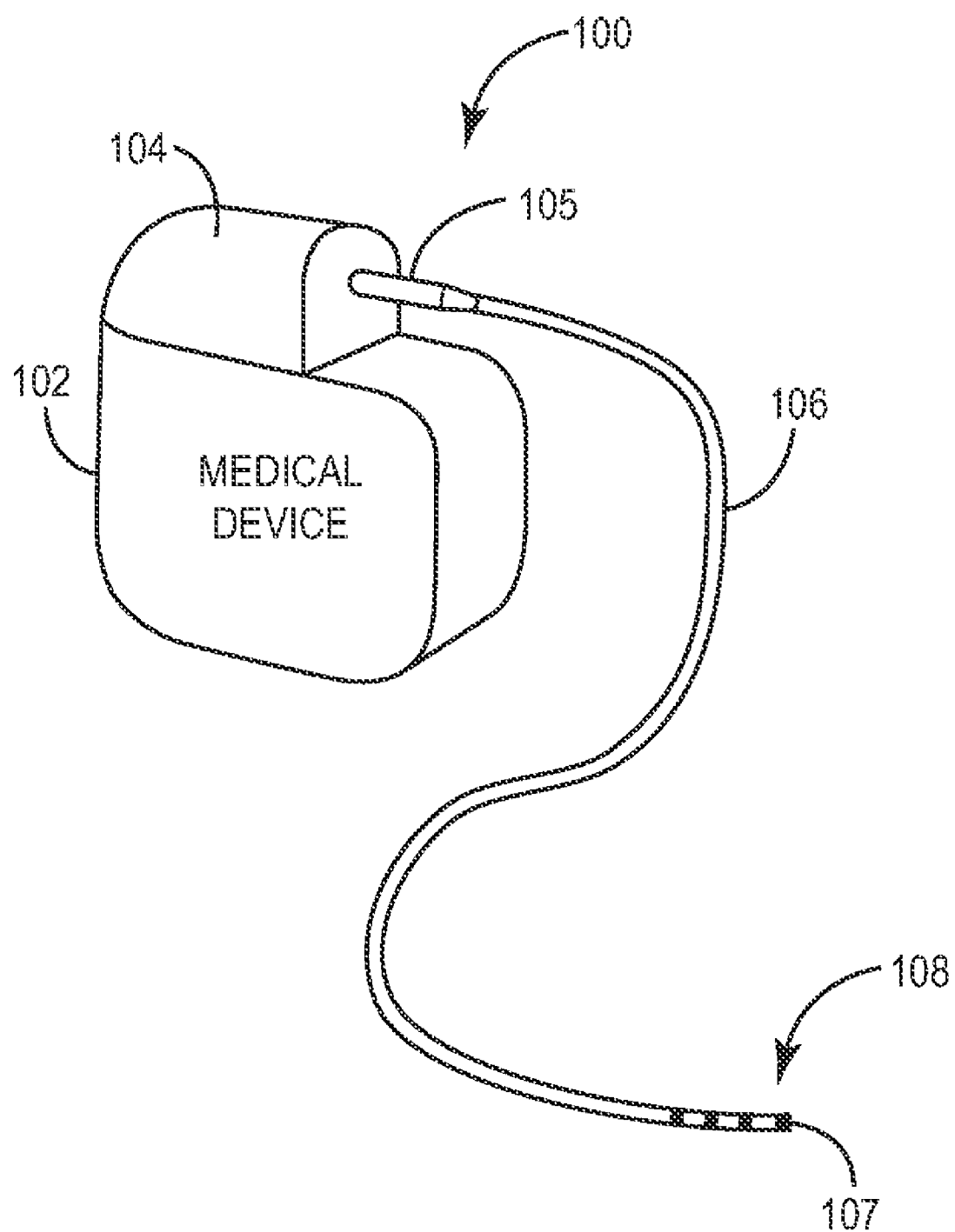
FIG. 1 is a conceptual perspective view of a medical device system including a medical device coupled to a lead according to an embodiment of the present invention.

FIG. 1 depicts a medical device system 100. A medical device system 100 includes a medical device housing 102 having a connector module 104 that electrically couples various internal electrical components of medical device housing 102 to a proximal end 105 of a medical lead 106 (also referred to as a MRI/RF shunted lead, or a shunted lead). A medical device system 100 may comprise any of a wide variety of medical devices that include one or more medical lead(s) 106 and circuitry coupled to the medical lead(s) 106. An exemplary medical device system 100 may take the form of an implantable cardiac pacemaker, an implantable cardioverter, an implantable defibrillator, an implantable cardiac pacemaker-cardioverter-defibrillator (PCD), a neurostimulator, or a muscle stimulator. Medical device system 100 may deliver, for example, pacing, cardioversion or defibrillation pulses to a patient via electrodes 108 disposed on distal ends 107 of one or more lead(s) 106. In other words, lead 106 may position one or more electrodes 108 with respect to various cardiac locations so that medical device system 100 can deliver pulses to the appropriate locations.

Figure 2:
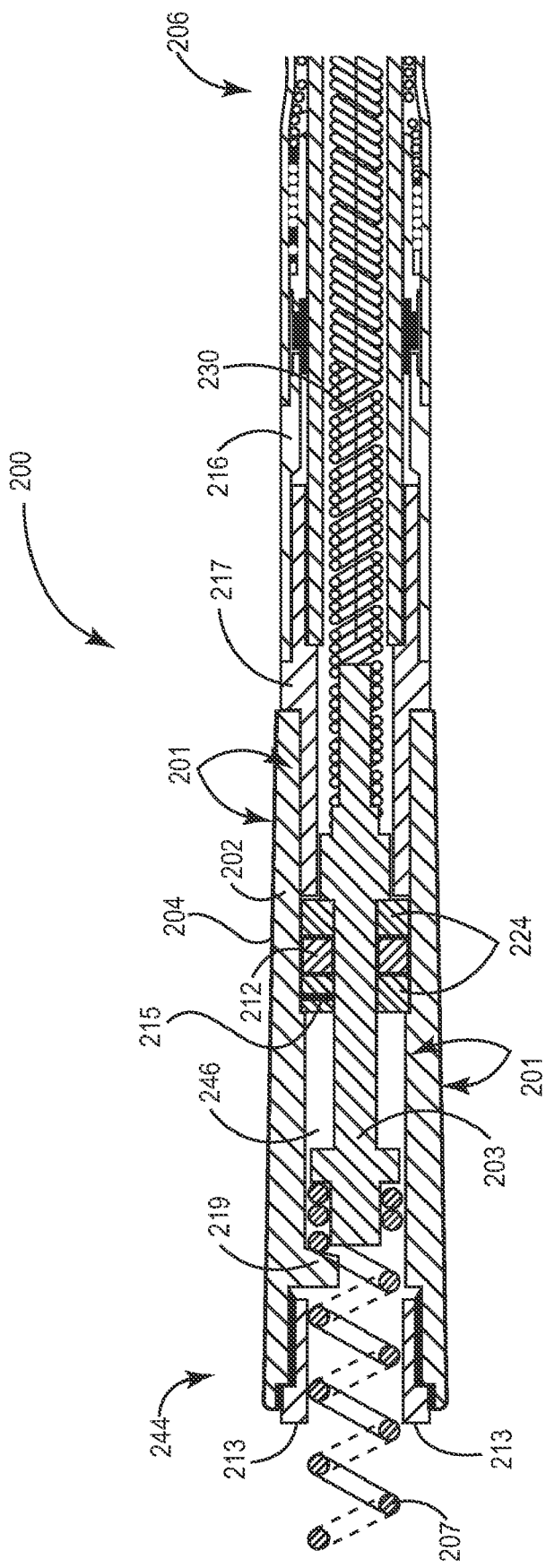
FIG. 2 is a cross-sectional view of an electrode assembly located at a distal end of a medical lead.

FIG. 2 depicts an electrode assembly 200 of a medical lead 106. Electrode assembly 200 optionally includes a sleeve head 201 coupled to an electrode 207 (also referred to as a tip electrode), a monolithic controlled-release device (MCRD) 213, a conductive electrode shaft 203, a conductive sealer 212, conductive rings 224, a ring electrode 216, and a nonconductive spacer 217. At a distal end 244 of electrode assembly 200, a sharpened distal tip (not shown) facilitates fixation of the distal end of helically shaped electrode 207 into tissue of a patient. The proximal end of electrode 207 is securely seated between MCRD 213, electrode shaft 203, and a securing member 219 that protrudes from an inner diameter of sleeve head 201. MCRD 213 provides chronic steroid elution to maintain a low pacing threshold for a medical device system 100.

Sleeve head 201 (optionally, a RF-shunted sleeve head) is electrically connected to a conductive electrode shaft 203 (e.g. platinum etc.) via two parallel conductive rings 224 (e.g. C-rings etc.) a conductive sealer 212 (also referred to as a sealing washer), and a magnetostrictive element 215 insulated with insulative layer 260. Insulative layer 260 is comprised of, for example, hydrolytically stable polyimide. At a proximal end 206 of electrode assembly 200, coil 230 is electrically coupled to conductive electrode shaft 203. In another embodiment, electrode shaft 203 is made of nonconductive polymeric material.

Sleeve head 201 comprises a conductive element 202 surrounded or at least partially covered by an insulating material 204 (also referred to as a dielectric material). In one embodiment, conductive element 202 is cylindrically shaped (e.g. ring, etc.) or may possess other suitable shapes. Exemplary dimensions for conductive element 202 include a diameter of about 6.5 French (Fr.) by about 9 millimeters (mm) in length, an outer diameter of about 82 mils and an inner diameter of about 62 mils. Conductive element 202, in one embodiment, includes an increased diameter at the distal end and a reduced diameter at the proximal end of the conductive element 202. The surface area of conductive element 202 is about 60 mm$^2$ which is much larger than the 5.5 mm$^2$ surface area of electrode 207. Conductive element 202 comprises materials that are chemically stable, biocompatible, and x-ray transparent. Exemplary material used to form conductive element 202 includes titanium, titanium alloy, conductive polymers, and/or other suitable materials.

Figure 3:
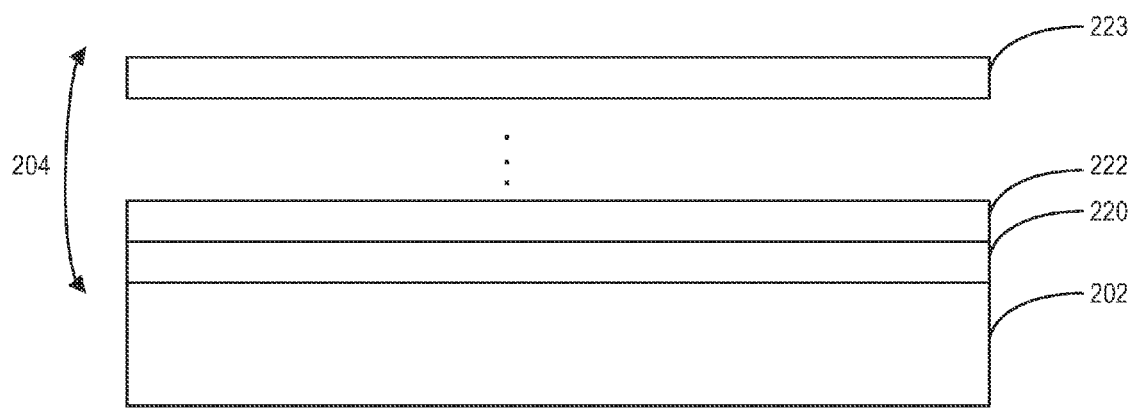
FIG. 3 depicts multiple layers of insulating material over a conductive element of the electrode assembly depicted in FIG. 2.
Figure 4A:
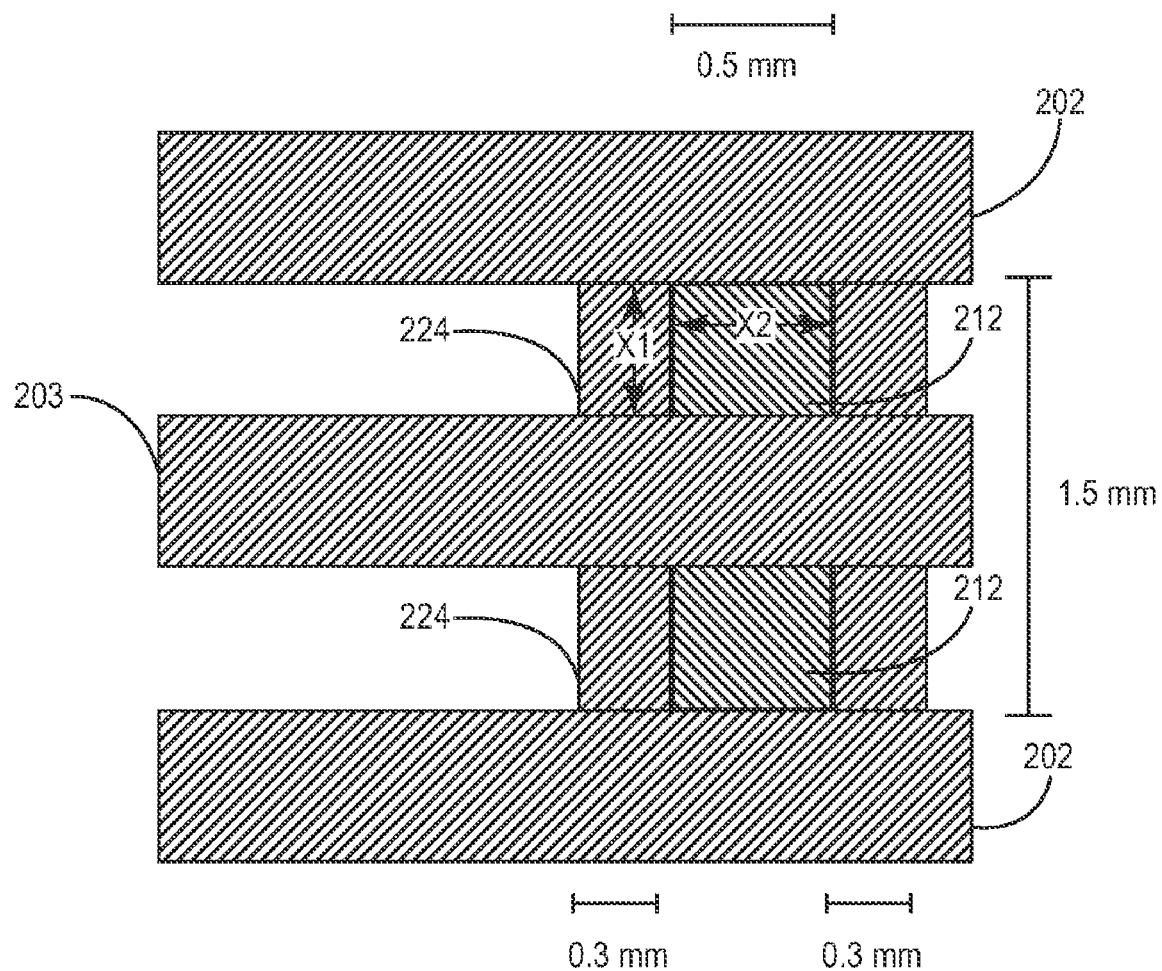
FIG. 4A depicts a cross-sectional view of a conductive ring coupled to a conductive sealer for the electrode assembly depicted in FIG. 2.
Figure 4B:
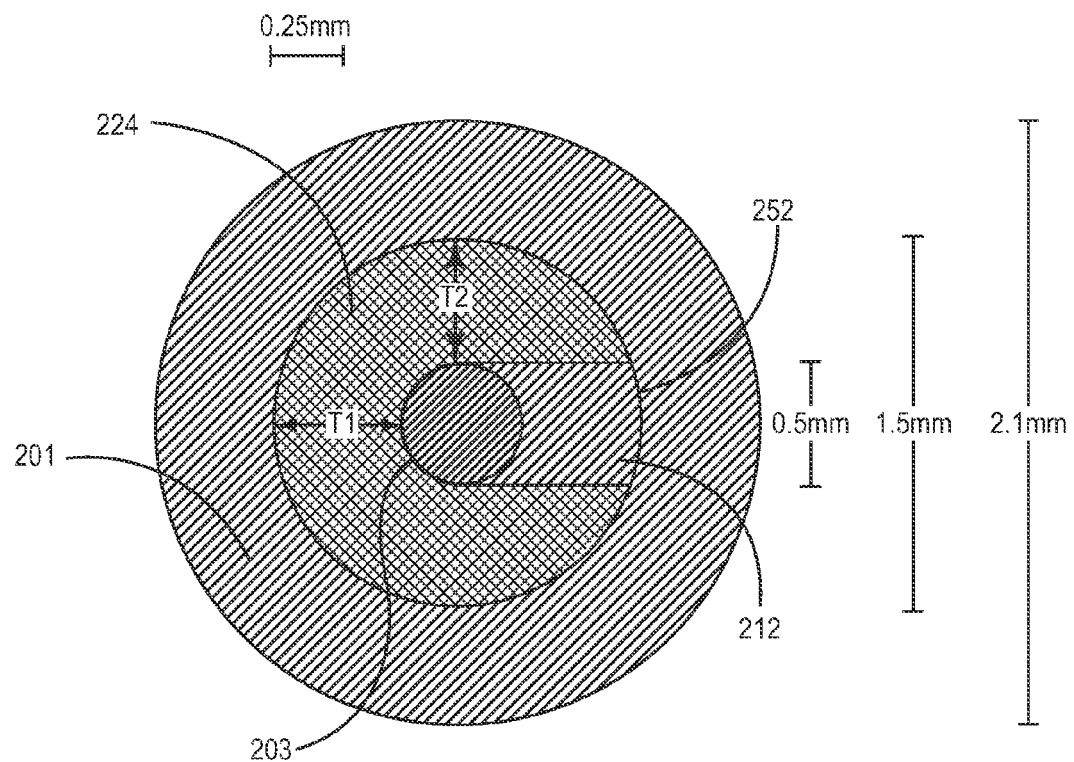
FIG. 4B depicts a top view of a conductive ring coupled to a conductive sealer for the electrode assembly depicted in FIG. 2.
Figure 4C:
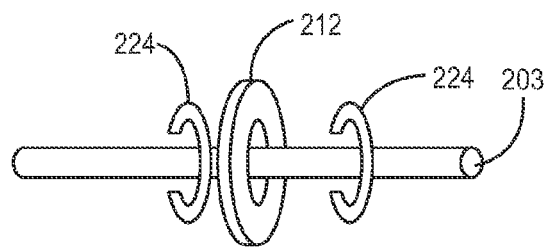
FIG. 4C depicts a cross-sectional view of conductive rings and a conductive sealer coupled to a shaft.
Figure 4D:
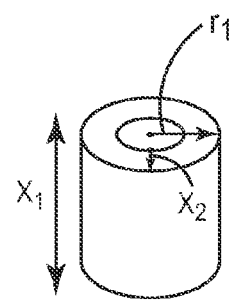
FIG. 4D depicts an angled view of a conductive sealer.

Referring to FIG. 3, insulative material 204 may be formed from a single layer or multiple layers such as first layer 220, second layer 222, and N layer 223, where N is a whole number that is less than 100, and is typically less than about 30 layers. Each layer may comprise different insulating materials, two or more different insulating materials, or the same insulating materials. Insulative material 204 includes a thickness from about 1 nanometer (nm) to about 1 millimeter (mm)) and extends from about 1 mm to about 20 mm along the length of conductive element 202. Insulative material 204 may be formed from any of a wide variety of insulating materials. Exemplary insulating material comprise at least one or more of parylene, polyamide, metal oxides, polyimide, urethane, silicone, tetrafluroethylene (ETFE), polytetrafluroethylene (PTFE), or the like. Parylene is the preferred insulating material 204. The preferred parylene is parylene C. Parylene C is formed through a dimer vacuum deposition process. The dimer is commercially available from Specialty Coating Systems located in Clear Lake, Wis. Numerous techniques may be employed to introduce insulating material 204 over the outside of sleeve head 201 and/or partially inside sleeve head 201. Exemplary techniques include chemical vapor deposition, dip coating, or thermal extrusion.

Conductive sealer 212 conducts current and also prevents fluid from passing through lumen 246. Referring to FIGS. 4A-4D, conductive sealer 212 is substantially ring (i.e. o-ring) or disk shaped but other suitable shapes may also be employed. In one embodiment, conductive sealer 212 is defined by X1, X2 and radius (r1). X1 ranges from about 0.1 mm to about 0.50 mm, X2 extends from about 0.1 mm to about 1.0 mm, and r1 extends from about 0.5 mm to about 1.0 mm. Curved end 252 extends to about 1.25 mm from the center of shaft 203 and includes a curve defined by a radius of about 0.5 mm.

Conductive sealer 212 comprises a polymer and a conductive polymer such as a conductive powder (e.g. carbon, carbon nanotube, silver, platinum etc.). The conductive polymer ranges from about 1% to about 25% of conductive sealer 212. The polymer (e.g. silicone etc.) is commercially available from Nusil Technology LLC, located in Carpinteria, Calif. Polyurethane is commercially available from The Polymer Technology Group Inc. located in Berkeley, Calif.

Conductive rings 224 are shaped, in one embodiment, as a C-ring to receive conductive sealer 212. Conductive rings 224 have an outer diameter of about 1.5 mm, an inner diameter of about 0.7 mm, and a thickness that ranges from about 0.25 mm (T1) to about 0.5 mm (T2). Conductive rings 224 are comprised of platinum or other suitable materials.

In one embodiment, magnetostrictive element 215 is coupled to at least one conductive ring 224. When lead 106 is exposed to MRI, magnetostrictive element 215a expands, which creates a larger surface area in which to dissipate the current induced in lead 106. In another embodiment, depicted in FIGS. 7A-7B, magnetostrictive element 215, is disposed between first and second segments 240a,b of electrode shaft 203. No gap exists between first and second segments 240a,b when MRI is not applied to lead 106. When lead 106 is exposed to MRI, first segment 240a expands and moves away from second segment 240b, thereby creating a gap 242. Gap 242 breaks the direct electrical connection between first and second segments 240a,b and the tip electrode 207. Instead, the current induced by MRI is shunted to a RF trap. In particular, high impedance inductor (L) 262, connected to electrode shaft 203, blocks the high frequency RF signals. L passes the low frequency pacing signals from one end to another end of the electrode shaft 203. The high frequency RF signals are shunted to magnetostrictive element 215.

Figure 5A:
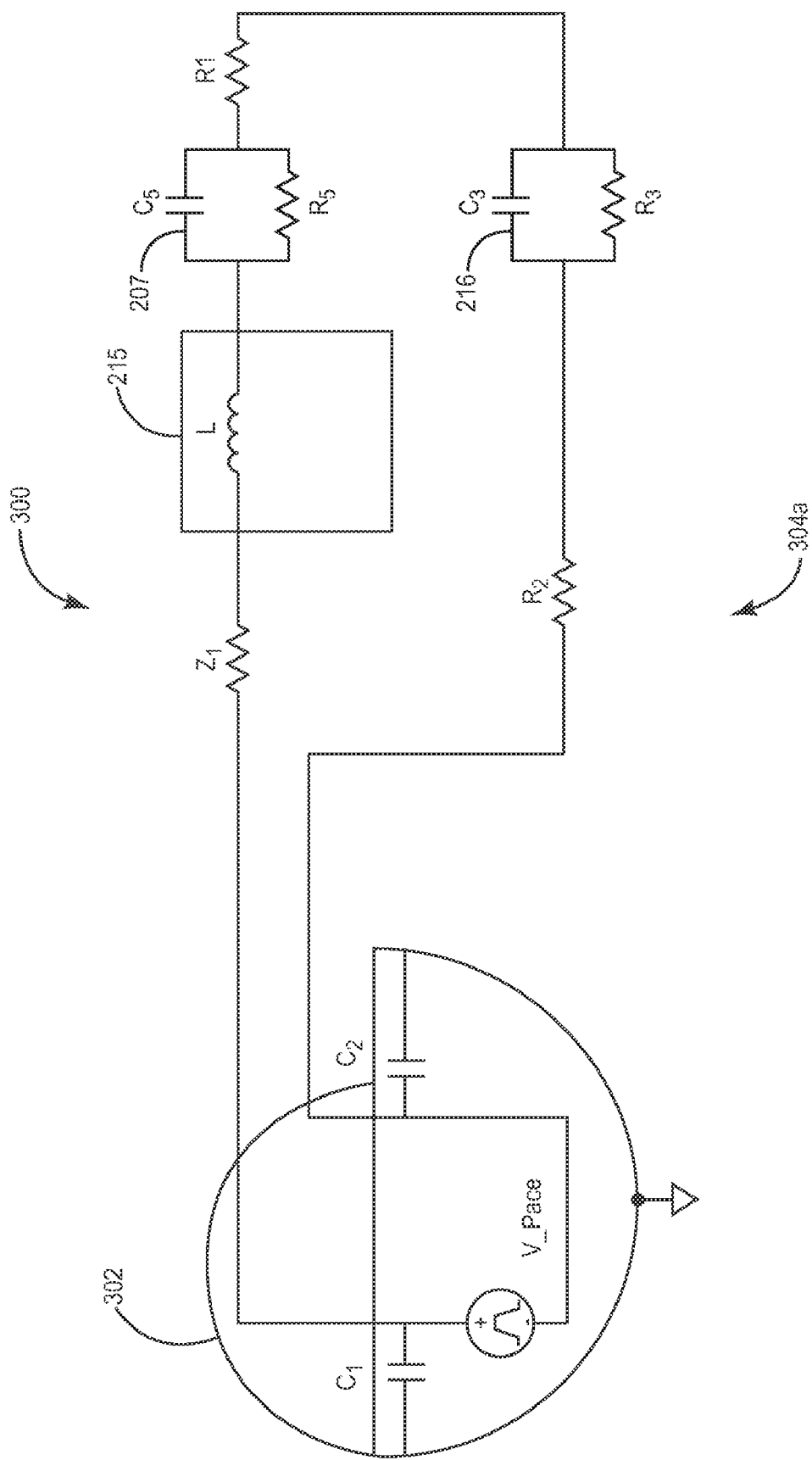
FIG. 5A is a schematic diagram of a simplified bipolar circuit for a medical device system under pacing and sensing conditions.

FIG. 5A depicts a simplified bipolar circuit 300 for a medical device system 100 during normal pacing conditions and when exposed to MRI. Pacing conditions typically involve low frequency signals (e.g. 1000 Hz). Circuit 300 includes an implantable medical device (IMD) circuit 302 (e.g. a pacemaker circuit, neurostimilator circuit etc.) connected to a bipolar shunted lead circuit 304. IMD circuit 302 comprises two filter capacitors C1 and C2 connected to housing 102. C1 and C2 filter high frequency electromagnetic interference (EMI) so that high frequency signals from a MRI machine do not affect the sensing operation of medical lead 106. Exemplary values for C1 is about 1 to 10 nanoFarad (nF) and C2 is 1-10 nF.

Bipolar shunted lead circuit 304a includes ring electrode 216, magnetostrictive element 215, and tip electrode 207. Capacitors C3 and C5 correspond to ring electrode 216, and tip electrode 207, respectively and inductor L is associated with magnetostrictive element 215. Resistors R1 and R2 represent the impedance created by tissue and/or blood of the patient. R3 and R5, along with capacitors C3 and C5, represent the electrode to tissue interface impedances. Generally, larger area electrodes result in larger values of capacitance and smaller values of resistance. Exemplary values for bipolar shunted lead circuit 304a include L C3 at 10 microF (uF), L is 4 uHenry, R3 is 100 Ohm (Ω), C5 is 1 uF, and R1 is 500Ω, and R5 is Ω.

Generally, under typical pacing conditions, pacing current flows from tip electrode 207 to ring electrode 216 and then returns to IMD circuit 302. Under a low frequency or direct current (DC) application, inductor L acts like a short circuit to a constant voltage across its terminals. A portion of the pacing current passes to the patient's tissue (e.g. heart tissue), represented as resistor R1, due to the large capacitance of C5 associated with tip electrode 207. Similarly, another portion of the pacing current passes to the patient's tissue, represented as resistor R3, due to the large capacitance of C3 associated with ring electrode 216. When lead 106 is exposed to MRI, current is induced, as depicted by the ghost lines.

Figure 5B:
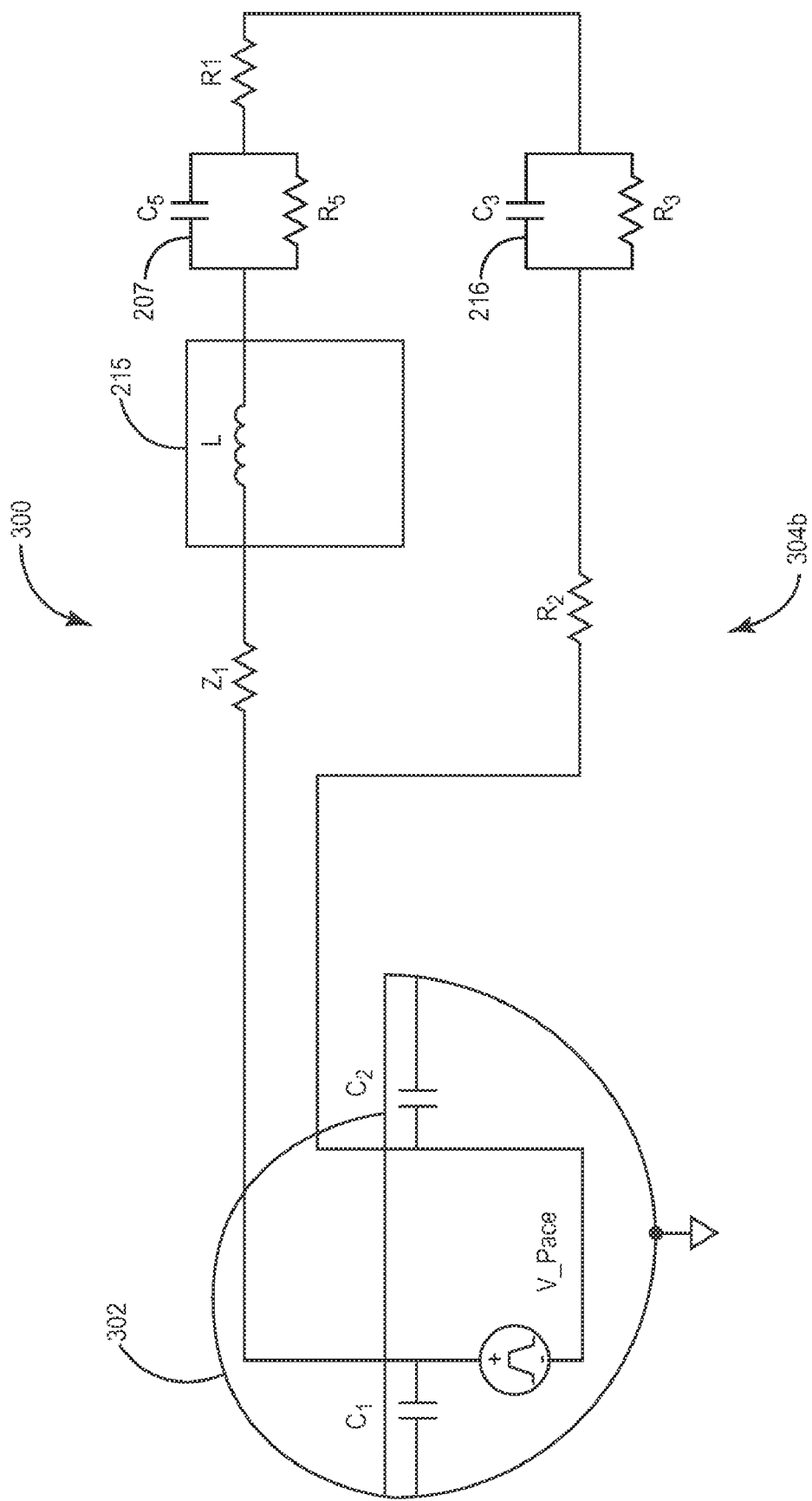
FIG. 5B is a schematic unipolar circuit for a medical device system.

FIG. 5B depicts a unipolar circuit 400. Unipolar circuit 400 includes IMD circuit 302 connected to unipolar shunted lead circuit 404. Unipolar lead circuit 404 includes magnetostrictive element 215, tip electrode 207, and resistors R1 and R2. Under MRI conditions, V-REF is induced and the resulting current is shunted to magnetostrictive element 515.

Figure 6A:
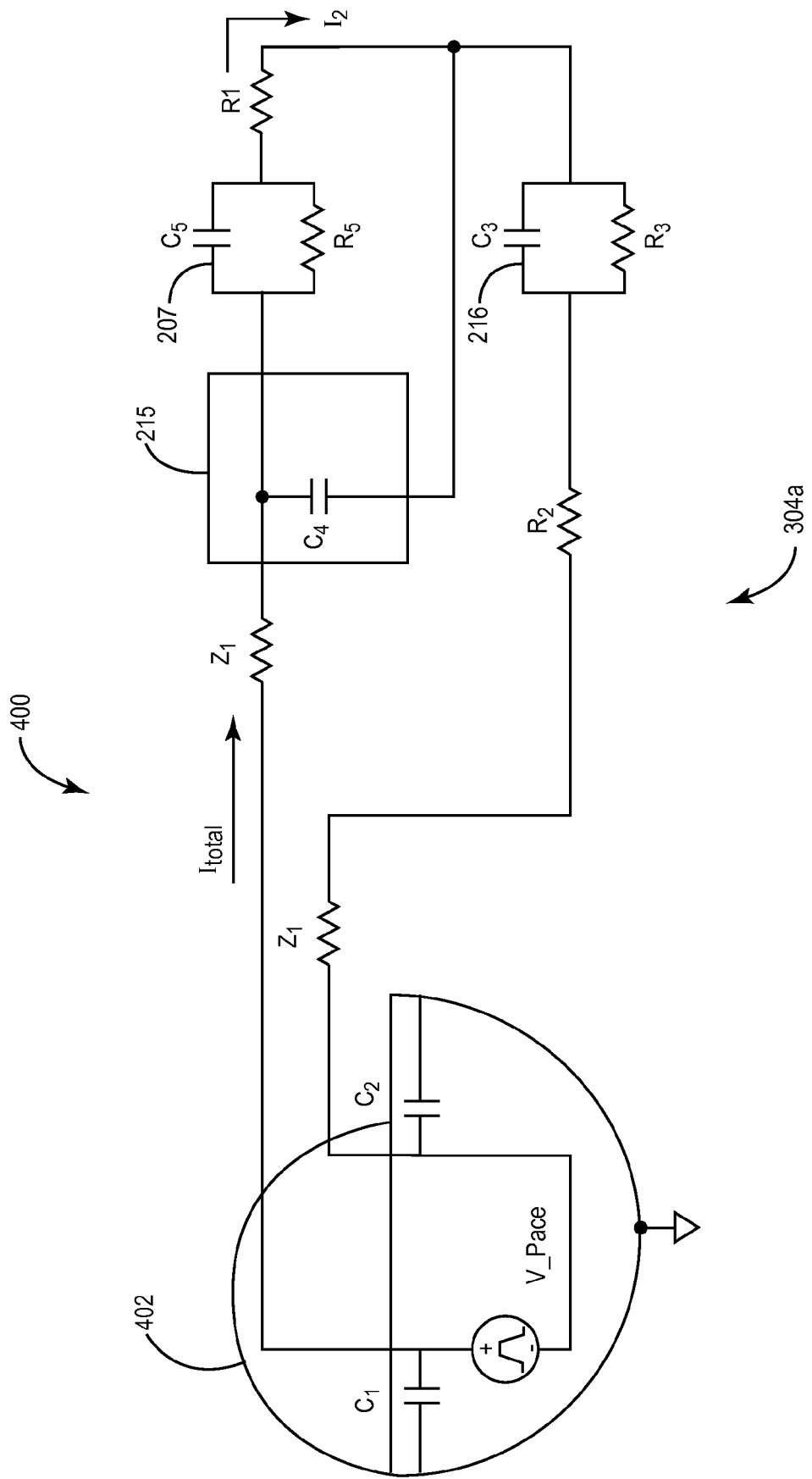
FIG. 6A is a schematic bipolar circuit for a simplified medical device system.
Figure 6B:
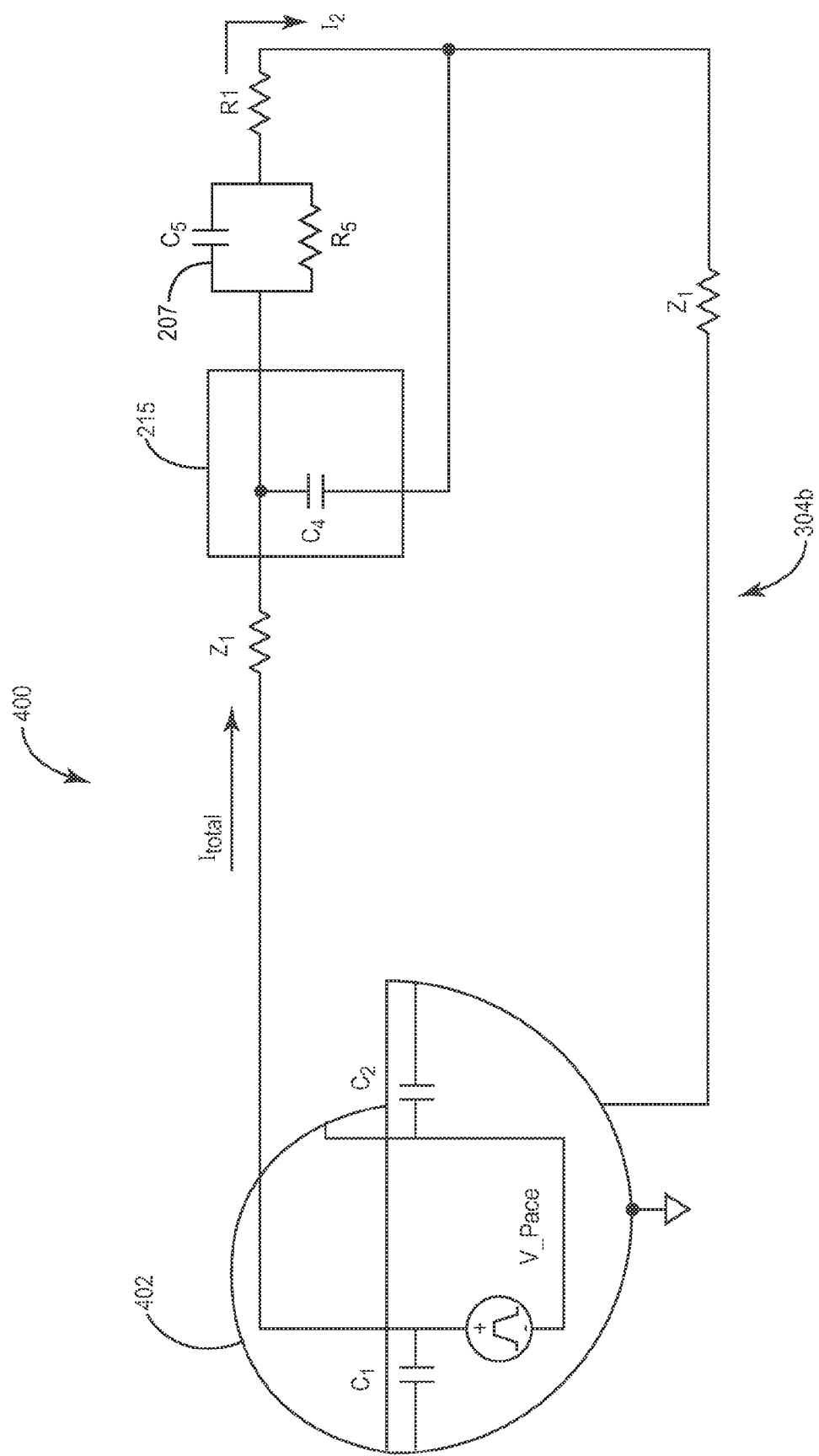
FIG. 6B is a schematic bipolar circuit of another simplified circuit for a medical device system.

FIGS. 6A-6B depicts a simplified circuit 400 for a medical device system 100 during pacing and MRI conditions, respectively. Circuit 400 includes an IMD circuit 402 (e.g. a pacemaker circuit, neurostimulator circuit etc.) and a bipolar shunted lead 304b. Circuit 400 includes the same elements as circuit 300 depicted in FIGS. 5A-5B, except magnetostrictive element 515 is coupled to a capacitor (C4). Magnetostrictive material 515 only acts as a switch to turn on and off C4 in circuit 400. In this embodiment, high frequency signals (i.e. from the MRI) pass to C4 whereas low frequency signals pass to and from tip electrode 207. C4 is shorted when exposed to high frequency signals. C4 acts as an "open circuit" when exposed to low frequency signals, which causes the pacing pulses to pass directly to tip electrode 207. An exemplary value for C4 is 1-10 uF.

Figure 8:
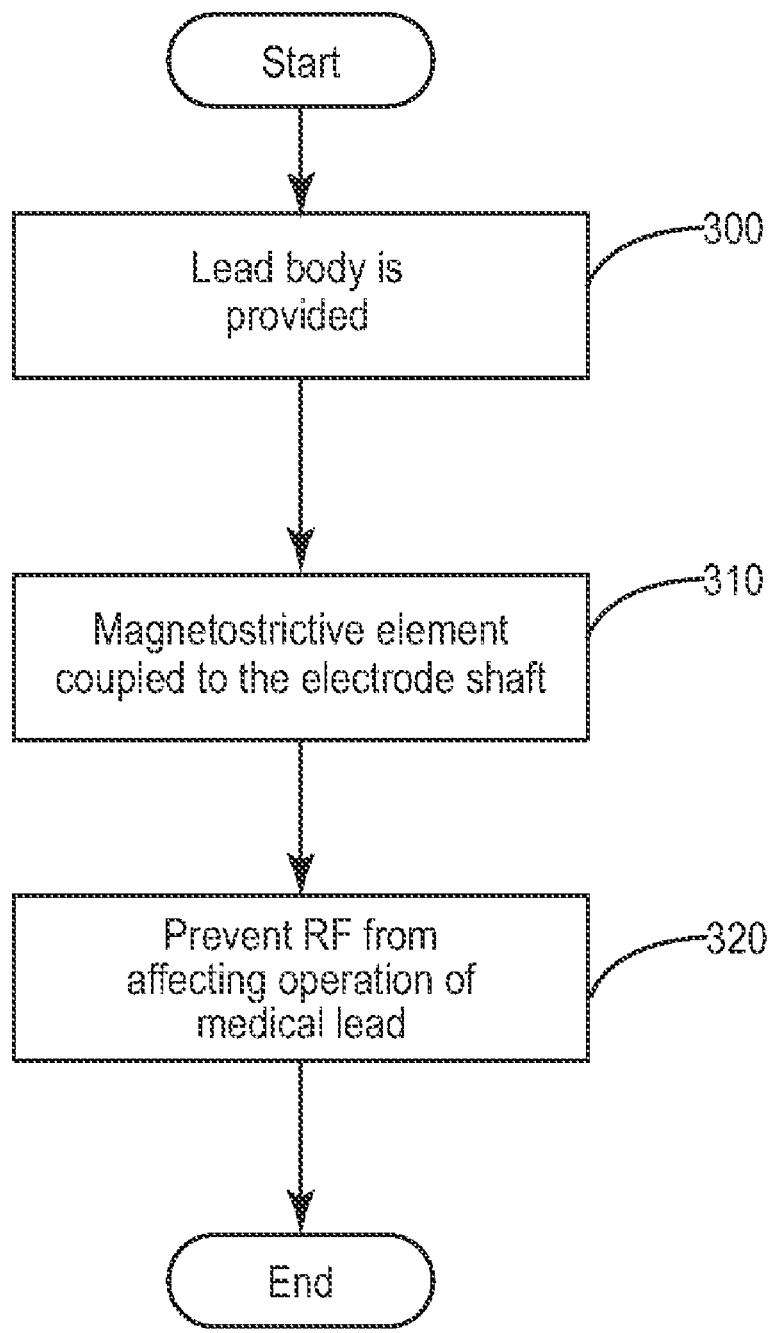
FIG. 8 is a flow diagram that depicts the method of producing an electrode assembly.

FIG. 8 is a flow diagram that depicts the method of producing a medical lead. At block 300, a lead body is provided. At block 310, a magnetostrictive element is inserted between a lead body and an electrode shaft. The magnetostrictive element is comprised of a ferromagnetic material (e.g. terfenol-D and galfenol). Terfenol-D is an alloy of terbium, dysprosium, and iron metals and has the largest room temperature magnetostriction of any material. In mechanical terms, a 2.5 inch diameter rod of terfenol-D is capable of generating over 50,000 pounds of dynamic force. At block 320, the RF is prevented from affecting the sensing operation of the medical lead. In one embodiment, the magnetostrictive element reduces by at least 80 percent the current, induced in the lead by the MRI. In another embodiment, the magnetostrictive element reduces by at least 50 percent the current induced by the MRI.

It is understood that the present invention is not limited for use in pacemakers, cardioverters of defibrillators. Other uses of the leads described herein may include uses in patient monitoring devices, or devices that integrate monitoring and stimulation features. In those cases, the leads may include sensors disposed on distal ends of the respective lead for sensing patient conditions.

The leads described herein may be used with a neurological device such as a deep-brain stimulation device or a spinal cord stimulation device. In those cases, the leads may be stereotactically probed into the brain to position electrodes for deep brain stimulation, or into the spine for spinal stimulation. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety medical devices that implement leads and circuitry coupled to the leads.

Various embodiments of the invention have been described. These and other embodiments are within the scope of the following claims. For example, electrode 207 may include variously shaped electrodes such as ring shaped or other suitable shapes. Additionally, skilled artisans appreciate that other dimensions may be used for the mechanical and electrical elements described herein.

The invention claimed is:

1. A medical device lead comprising:
    a lead body;
    a first conductive electrode;
    an electrode shaft disposed inside of the lead body and coupled to the first electrode;
    a second conductive electrode; and
    a magnetostrictive element coupled between the electrode shaft and the second electrode, wherein the magnetostrictive element expands to contact the electrode shaft to the second electrode when exposed to a magnetic field to dissipate at least a portion of an electric current induced in the lead by a magnetic resonance imaging (MRI) device via the second electrode.

2. The medical device lead of claim 1, wherein the magnetostrictive element comprises at least one of terfenol-D and galfenol.

3. The medical device lead of claim 1, wherein the second electrode comprises:
    a conductive element; and
    an insulating material that covers at least an outside portion of the conductive element.

4. The medical device lead of claim 1, wherein the magnetostrictive element is disposed in or near conductive rings that are coupled to the electrode shaft.

5. The medical device lead of claim 1, wherein the second electrode has a surface area that is at least approximately ten times larger than a surface area of the first electrode.

6. The medical device lead of claim 1, further comprising a coiled conductor within the lead body that is electrically coupled to the electrode shaft, wherein a proximal end of the lead body is configured to electrically couple the coiled conductor to electrical components of an implantable medical device.

7. A method of forming a medical electrical lead comprising:

providing a lead body;
coupling a magnetostrictive element to an electrode shaft; and
inserting the magnetostrictive element and the electrode shaft into the lead body such that the electrode shaft is electrically coupled to a first electrode and the magnetostrictive element is located between the electrode shaft and a second electrode such that the magnetostrictive element expands to contact the electrode shaft to the second electrode when exposed to a magnetic field to dissipate at least a portion of an electric current induced in the lead by a magnetic resonance imaging (MRI) device.

8. The method of claim 7, wherein the magnetostrictive element comprises one of galfenol and terfenol-D.

9. A medical device system comprising:
an implantable medical device that includes:
a housing, and
electrical components within the housing that generate electrical stimulation therapy; and
an electrical stimulation lead that includes:
a lead body,
a first conductive electrode located at a distal end of the leady body,
a conductive electrode shaft within the leady body and electrically coupled to the electrode,
a coiled conductor within the lead body and electrically coupled to the electrode shaft, wherein a proximal end of the lead body is configured to electrically couple the coiled conductor to the electrical components of the implantable medical device,
a second conductive electrode
a magnetostrictive element coupled between the electrode shaft and the second electrode, wherein the magnetostrictive element expands to contact the electrode shaft to the second electrode when exposed to a magnetic field to dissipate at least a portion of an electric current induced in the coiled conductor by a magnetic resonance imaging (MRI) device via the second electrode.

10. The medical device system of claim 9, wherein the second electrode has a surface area that is at least approximately ten times larger than a surface area of the first electrode.

11. The medical device system of claim 9, wherein the magnetostrictive element is disposed in or near conductive rings that are coupled to the electrode shaft.

12. The medical device system of claim 9, wherein the magnetostrictive element comprises at least one of terfenol-D and galfenol.

13. The medical device system of claim 9, wherein the second electrode comprises:
a conductive element; and
an insulating material that covers at least an outside portion of the conductive element.

* * * * *